United States Patent [19]
Pillai et al.

[11] Patent Number: 5,476,661
[45] Date of Patent: Dec. 19, 1995

[54] COMPOSITIONS FOR TOPICAL APPLICATION TO SKIN, HAIR AND NAILS

[75] Inventors: Sreekumar Pillai, Wayne; Suk H. Cho, Bogota; Anthony V. Rawlings, Wyckoff, all of N.J.

[73] Assignee: Elizabeth Arden Co., Division of Conopco, Inc., New York, N.Y.

[21] Appl. No.: 326,994

[22] Filed: Oct. 21, 1994

[51] Int. Cl.$^6$ .............................. A61K 7/48; A61K 7/06; A61K 7/04
[52] U.S. Cl. .............. 424/401; 424/61; 424/701; 514/844; 514/846; 514/847
[58] Field of Search ............. 424/401, 61, 70.1; 514/844, 846, 847

[56] References Cited

U.S. PATENT DOCUMENTS

| | | | |
|---|---|---|---|
| 4,778,823 | 10/1988 | Kawamata et al. | 514/625 |
| 4,985,547 | 1/1991 | Yano et al. | 536/41 |
| 5,175,321 | 12/1992 | Ohashi et al. | 554/63 |
| 5,198,210 | 3/1993 | Critchley et al. | 424/78.03 |
| 5,206,020 | 4/1993 | Critchley et al. | 424/401 |

FOREIGN PATENT DOCUMENTS

| | | |
|---|---|---|
| 0512814 | 11/1992 | European Pat. Off. . |
| WO91/19479 | 12/1991 | WIPO . |

OTHER PUBLICATIONS

Pillai et al., "Epidermal Vitamin D Metabolism, Function, and Regulation", *Advances In Lipid Research*, vol. 24, (1991), pp. 321–341.

Bikle et al., "1,25–Dihydroxyvitamin $D_3$ Production by Human Keratinocytes", *The Journal of Clinical Investigation, Inc.*, vol. 78, (Aug. 1986), pp. 557–566.

Pillai et al., "1,25–Dihydroxyvitamin D Production and Receptor Binding in Human Keratinocytes Varies with Differentiation", *The Journal of Biological Chemistry*, vol. 263, No. 11, (Apr. 15, 1988), pp. 5390–5395.

Hashimoto et al., "Growth–inhibitory Effects of 1,25–Dihydroxyvitamin $D_3$ on Normal and Psoriatic Keratinocytes", *British Journal of Dermatology*, (1990), vol. 123, pp. 93–98.

Morimoto et al., "Topical Administration of 1,25–Dihydroxyvitamin $D_3$ for Psoriasis: Report of Five Cases", *Calcif Tissue Int.*, vol. 38, (1986), pp. 119–122.

MacLaughlin et al., "Cultured Human Keratinocyctes Cannot Metabolize Vitamin $D_3$ to 25–hydroxyvitamin $D_3$", *Federation of European Biochemical Societies*, vol. 282, No. 2, (May 1991), pp. 409–411.

Holick, M. F. in "Cutaneous Aging" (edited by A. Kligman), pp. 223–246, Univ. of Tokyo Press, Tokyo, 1988.

Bikle et al., "Squamous Carcinoma Cell Lines Produce 1,25–Dihydroxyvitamin D, but Fail to Respond to Its Prodifferentiating Effect", *The Society for Investigative Dermatology, Inc.*, (1991), p. 435.

Okazaki et al., reported in "Role of Ceramide as a Lipid Mediator of 1α,25–Dihydroxyvitamin $D_3$–induced HL–60 Cell Differentiation", *The Journal of Biological Chemistry*, vol. 265, No. 26, Sep. 15, 1990, pp. 15823–15831.

Calcif Tissue Int, vol. 38 pp. 119–122 (1986).

*Primary Examiner*—Jyothsna Venkat
*Attorney, Agent, or Firm*—Rimma Mitelman

[57] ABSTRACT

Compositions for treating skin, hair and nails which contain 25-hydroxycalciferol in combination with a lipid ingredient. The compositions avoid the toxic effects of 1,25-dihydroxycalciferol, yet attain keratinocyte differentiation and provide additional benefits. Also disclosed is a method of improving or preventing the appearance of wrinkled, flaky, aged, photodamaged skin by applying to skin a composition containing in a cosmetically acceptable vehicle 25-hydroxycalciferol and a lipid ingredient.

5 Claims, No Drawings

COMPOSITIONS FOR TOPICAL APPLICATION TO SKIN, HAIR AND NAILS

FIELD OF THE INVENTION

The invention relates to compositions for topical application to human skin, hair, and nails, which compositions contain 25-hydroxycholecalciferol in combination with a lipid component and to methods of using the compositions for treatment and conditioning of skin.

BACKGROUND OF THE INVENTION

The top layer of human skin or the epidermis is composed of many different cell types including keratinocytes, melanocytes and langerhans cells. Keratinocytes are the major cell type of the epidermis (75–80% of the total number of cells in the human epidermis). Within the epidermis the keratinocytes reside in four distinct stages of differentiation. The basal layer rests on the basal lamina separating epidermis from the dermis. These cells are large columnar rapidly proliferating cells. These basal cells migrate upward within the epidermis, initiated by the process of differentiation. The layer above the basal cells is the spinous layer. The cells in the spinous layer initiate the production of proteins characteristic of the differentiated epidermis. The granular layer, lying above the spinous layer, is characterized by electron-dense granules. This layer is responsible for the synthesis of lipid molecules required for the formation of the water impermeable barrier of the skin. The topmost layer of the skin, the stratum corneum, is formed from the granular layer by the destruction of cellular organelles. The cells in the stratum corneum, corneocytes, contain extensively cross-linked proteins, surrounded by a highly resistant cell envelope. The corneocytes are embedded in a bed of specific lipid structures (analogous to bricks on a bed of mortar) and this structure provides the protective barrier for the skin. The outermost layer of corneocytes is peeled off from the skin during the normal process of desquamation. Differentiation of the epidermal keratinocytes is the driving force for the normal desquamation process to occur. Epidermal differentiation is important for providing the essential function of the skin, namely to provide a protective barrier against the outside environment and to prevent loss of water from the body. The basal cells which have the highest rate of growth, are the least differentiated. The most differentiated cells of the stratum corneum do not have the ability to grow.

Initiation of differentiation of keratinocytes is accompanied by inhibition of their growth. The rate of synthesis of DNA determined by the incorporation of radiolabeled substrate [$^3$H] thymidine, is an indicator of the rate of growth of the cells. A decrease in DNA synthesis therefore indicates decrease in growth and increase in differentiation of keratinocytes.

The present invention is based, in part, on the discovery that a combination of two specific active ingredients, namely 25-hydroxycholecalciferol and short chain lipids, results in synergistic increase in differentiation, which in turn results in increased benefits to skin, such as improved conditioning, improved youthful appearance, decrease in wrinkle appearance, moisturizing, and treatment of photodamaged skin and various skin disorders.

Vitamin $D_3$ is produced in the skin of mammals as the result of irradiation which converts 7-dehydrocholesterol into vitamin $D_3$ in the presence of sufficient sunshine. Vitamin $D_3$ is then metabolized into active biological metabolites. The majority of vitamin $D_3$ is taken up by liver where it is hydroxylated at C-25. The resulting 25-hydroxycholecalciferol (hereinafter "25-OH-$D_3$") is then transported to various target organs where further hydroxylation takes place at C-1 or C-24. Several published studies establish that skin is one of the organs in which synthesis of 1,25-dihydroxycholecalciferol (hereinafter "1,25-(OH)$_2$D$_3$") and 24,25-dihydroxycholecalciferol from 25-OH-$D_3$ occurs. See e.g., Bikle et al., "1,25-Dihydroxyvitamin $D_3$ Production by Human Keratinocytes", *The Journal of Clinical Investigation, Inc.*, Volume 78, (August 1986), pp. 557–566.

1,25-(OH)$_2$D$_3$ is the major biologically active metabolite of vitamin $D_3$. 1,25-(OH)$_2$D$_3$ plays a central role in regulating blood calcium levels by increasing bone resorption and calcium absorption from intestine. Recent studies indicate that exogenous or endogenous 1,25-(OH)$_2$D$_3$ inhibits DNA synthesis (i.e., inhibits growth) and induces differentiation of keratinocytes. See e.g., Pillai et al. "1,25-Dihydroxyvitamin D Production and Receptor Binding in Human Keratinocytes Varies with Differentiation" *The Journal of Biological Chemistry*, Vol. 263, No. 11, (Apr. 15, 1988), pp. 5390–95; and Hashimoto et al., "Growth-inhibitory effects of 1,25-Dihydroxyvitamin $D_3$ on Normal and Psoriatic Keratinocytes" *British Journal of Dermatology* (1990) Vol. 123, pp. 93–98. Topical compositions containing 1,25-(OH)$_2$D$_3$, particularly for psoriasis treatment, are known. See e.g., Morimoto et al., "Topical Administration of 1,25-Dihydroxyvitamin $D_3$ for Psoriasis: Report of Five Cases", *Calcif Tissue Int.*, Vol. 38, (1986), pp. 119–22. See also European Patent Application 512,814 which describes cosmetic compositions containing 1-hydroxycholecalciferol and/or 1,25-(OH)$_2$D$_3$. The composition is said to prevent the damaging effects of ultra-violet light on skin and to promote the repair of photodamaged skin.

Vitamin $D_3$ per se is biologically inactive. Vitamin $D_3$ when applied topically to skin neither has keratinocyte prodifferentiating activity nor is it converted in the skin to 25-OH-$D_3$ derivative which is a necessary precursor of 1,25-(OH)$_2$D$_3$ metabolite. See MacLaughlin et al., "Cultured Human Keratinocytes Cannot Metabolize Vitamin $D_3$ to 25-hydroxyvitamin $D_3$" *Federation of European Biochemical Societies*, Vol. 282, No. 2, ;(May 1991), pp. 409–411. Thus, although numerous cosmetic compositions containing vitamin $D_3$ are known and are available commercially, such compositions do not provide the benefit of 1,25-(OH)$_2$D$_3$ induced keratinocyte differentiation.

Unfortunately, topical application of 1,25-(OH)$_2$D$_3$ must be carefully controlled, because 1,25-(OH)$_2$D$_3$ applied topically increases blood level of 1,25-(OH)$_2$D$_3$. The normal concentration of 1,25-(OH)$_2$D$_3$ in blood is $10^{-12}$M. Higher levels of 1,25-(OH)$_2$D$_3$ increase blood calcium levels and may cause heart problems, muscle weakness and contraction which may be fatal. When 1,25-(OH)$_2$D$_3$ is produced endogenously the problem of toxicity does not occur, because the enzyme that produces 1,25-(OH)$_2$D$_3$ from 25-OH-$D_3$ is shut off when endogenous levels of 1,25-(OH)$_2$D$_3$ are at normal circulating levels which is well below toxic levels.

Thus, it is desirable to maintain optimum endogenous production of 1,25-(OH)$_2$D$_3$ in skin in order to promote keratinocyte differentiation and, in turn, to maintain or promote a healthy, smooth, young-looking skin. The endogenous production of 1,25-(OH)$_2$D$_3$ in the skin is limited, however, by the level of vitamin $D_3$ produced in the skin and by the blood levels of 25-OH-$D_3$. Several factors, such as increased skin pigmentation, reduced sunlight, and aging, all decrease the capacity of human skin to produce vitamin $D_3$. See Holick, M. F. in "Cutaneous Aging" (edited by A. Kligman), pp. 223–246, Univ. of Tokyo Press, Tokyo, 1988.

It is known that exogenously applied 25-OH-$D_3$ is converted to 1,25-$(OH)_2D_3$ in keratinocyte cultures. Bikle et al. reported in "Squamous Carcinoma Cell Lines Produce 1,25-Dihydroxyvitamin D, but Fail to Respond to Its Prodifferentiating Effect", *The Society for Investigative Dermatology, Inc.*, (1991), p. 435, that keratinocytes need not depend on exogenously added 1,25-$(OH)_2D_3$ as they can rapidly convert exogenously added 25-OH-$D_3$ to 1,25-$(OH)_2D_3$. It is desirable, however, to maximize the pro-differentiating effect of 25-OH-$D_3$. Additionally, it is desirable to avoid fast uptake of active ingredients by skin cells in order to attain a prolonged exposure of skin cells to active ingredients. Unfortunately, exogenously added 1,25-$(OH)_2D_3$ is rapidly degraded within the skin cells. See Bikle et al., "1,25-Dihydroxyvitamin $D_3$ Production by Human Keratinocytes", *The Journal of Clinical Investigation, Inc.*, Volume 78, (August 1986), pp. 557–566. Slow uptake of active ingredients also minimizes cost of production and maximizes effectiveness of compositions by providing skin cells with steady state levels of ingredients for prolonged periods of time.

The present invention is based at least in part on the discovery that the addition of certain lipids to 25-OH-$D_3$ results in a synergistic increase in keratinocyte differentiation. The inventive compositions avoid the toxic effects of 1,25-$(OH)_2D_3$ and increase substantially the prodifferentiating activity of 25-OH-$D_3$. It has also been found as part of the present invention that the application to skin of 25-OH-$D_3$ in place of 1,25-$(OH)_2D_3$ results in slower uptake of the active ingredients by skin cells.

Cosmetic compositions are known which utilize ceramides (lipids found in skin) and pseudoceramides (synthetic molecules resembling ceramides) to control water loss and/or to repair damaged (e.g., dry, flaky, chapped, wrinkled) skin by replacing the skin's natural lipids. See, for example, U.S. Pat. Nos. 5,206,020 (Critchley et al.), 5,198,210 (Critchley et al.), 5,175,321 (Ohashi et al.), 4,985,547 (Yano et al.), 4,778,823 (Kawamata et al.), and European Patent Application 556,957. Ceramides alone do not induce keratinocyte differentiation, except at higher levels. The incentive exists, however, to keep ceramides' level in a formulation at a minimum due to high cost of ceramides.

Okazaki et al. reported in "Role of Ceramide as a Lipid Mediator of 1α,25-Dihydroxyvitamin $D_3$-induced HL-60 Cell Differentiation", *The Journal of Biological Chemistry*, Vol. 265, No. 26, Sep. 15, 1990. pp. 115823–31, that cell-permeable ceramides with shorter N-acyl chains induce HL-60 cell (human myelocytic leukemia cells) differentiation at subthreshold concentrations of 1,25-$(OH)_2D_3$. In this regard, it should be noted that while lipids are also included in the inventive compositions, HL-60 cells (pathological tumor cells found in blood) and keratinocytes (normal cells found in skin) are so different from each other in function, their differentiation pathways and biological environment are so diverse and the principles and skills required in formulating cosmetic compositions and anti-tumor compositions are so distinct, that it is difficult to extend the teachings in one of the arts to the other. The fact that some agent induces differentiation of HL-60 cells is not necessarily indicative that the same agent will induce differentiation of keratinocytes. For example, retinoic acid induces differentiation of HL-60 cells but prevents differentiation of keratinocytes. Furthermore, in the present invention a lipid ingredient is employed in combination with 25-OH-$D_3$, not 1,25-$(OH)_2D_3$. Topical application of 1,25-$(OH)_2D_3$ is problematic for reasons discussed above.

Accordingly, it is an object of the present invention to provide compositions for treatment of skin, while avoiding the disadvantages of prior art.

It is another object of the present invention to provide a skin treatment composition containing 25-OH-$D_3$ in combination with an ingredient which enhances the keratinocytes prodifferentiating activity of 25-OH-$D_3$.

It is yet another object of the invention to provide a skin treatment composition which maximizes the prodifferentiating activity of 1,25-$(OH)_2D_3$ while avoiding the toxic effects of 1,25-$(OH)_2D_3$.

It is still another object of the invention to provide a skin treatment composition which is taken up by skin cells slowly.

It is another object of the invention to provide a method for treating or preventing the appearance of wrinkled, flaky, aged, photodamaged skin or skin disorders.

These and other objects of the invention will become more apparent from the detailed description and examples which follow.

SUMMARY OF THE INVENTION

The above objects are attained by the present invention which includes, in part, a composition containing:

(i) from about 0.000001% to about 10 wt. % of 25-OH-$D_3$;

(ii) from about 0.0001% to about 50 wt. % of a lipid material selected from the group consisting of ceramides, pseudoceramides, neoceramides, and mixtures thereof; and (iii) a cosmetically acceptable vehicle for 25-OH-$D_3$ and the lipid material.

Preferably, the ratio of the lipid ingredient to 25-OH-$D_3$ is in the range of from about 1:1 to about 250:1, most preferably the ratio is about 100:1.

The vehicle enables the 25-OH-$D_3$ and the lipid material to be dispersed onto the skin and distributed therein. According to the preferred embodiment of the invention, 25-OH-$D_3$ is employed in combination with the lipid material selected from short to medium chain (i.e., $C_1$–$C_{16}$) ceramides, pseudoceramides and neoceramides, most preferably $C_1$–$C_{10}$ (i.e., R in ceramides of Formula II or $R_6$ in pseudoceramides of Formula III or $R_{11}$ in neoceramides of Formula IV, contains from 1 to 10 carbon atoms), in order to attain a synergistic; keratinocyte prodifferentiating activity.

The use of 25-OH-$D_3$ instead of 1,25-$(OH)_2D_3$ is advantageous. In addition to avoiding the toxic effects of 1,25-$(OH)_2D_3$, the application of 25-OH-$D_3$ to skin resulted in slower uptake of 25-OH-$D_3$ by skin cells when compared to the uptake of 1,25-$(OH)_2D_3$. The slower uptake is beneficial in that it results in a prolonged exposure of skin cells to active ingredients preventing rapid degradation of active ingredients and preventing toxic effects, yet allowing greater differentiation benefits.

The present invention also includes a method of improving or preventing the appearance of wrinkled, flaky, aged, photodamaged skin and treating skin disorders, which method includes applying to the skin a composition containing 25-OH-$D_3$ and a lipid ingredient.

Compositions of the invention are intended for topical application to mammalian skin which is already in dry, flaky, wrinkled, aged, photodamaged condition or which suffers from a skin disorder, or, in the alternative, the inventive compositions may be applied prophylactically to normal healthy skin to prevent or reduce the deteriorative changes.

DETAILED DESCRIPTION OF THE INVENTION

The inventive compositions contain, as a first essential ingredient, 25-OH-D$_3$ having Formula I:

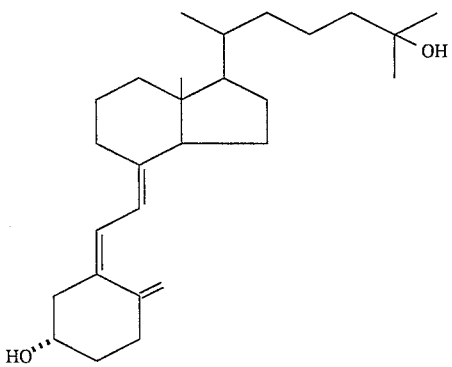

The composition according to the invention includes an effective amount of 25-OH-D$_3$ to induce differentiation. The particular amount of 25-OH-D$_3$ depends on the identity of other ingredients in a final composition and the condition of the skin. In general, the amount of 25-OH-D$_3$ is in the range of from about 0.000001% to about 10% by weight of the composition. Preferably, in order to lower cost and maximize the synergistic effect, the amount of 25-OH-D$_3$ is in the range of from about 0.00001 to about 1%, most preferably in the range of from 0.00001 to 0.1%.

Lipid Component

The second essential ingredient of the inventive compositions is a lipid. The lipid component is chosen from ceramides, pseudoceramides, neoceramides and mixtures thereof.

Ceramides

Ceramides are preferably selected from ceramides having the general structure (II):

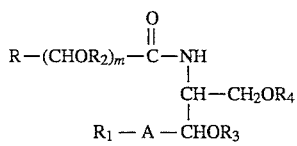

where

A represents —CH$_2$—; —CHOR$_5$—; —CH=CH— or —CHOY—;

R represents a subgroup (2) or a linear or branched saturated or unsaturated, aliphatic hydrocarbon group having from 1 to 50 carbon atoms which may contain a hydroxyl group:

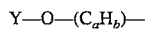 (2)

R$_1$ represents a linear or branched, saturated or unsaturated, hydroxylated or non-hydroxylated aliphatic hydrocarbon group having from 8 to 28 carbon atoms or a phenyl group;

R$_2$, R$_3$ and R$_5$ individually represent H, a phosphate group or a sulphate group;

R$_4$ represents H, a phosphate group, a sulphate group or a sugar group;

a is an integer of from 1 to 49;

b is an integer of from 2 to 98;

m is 0 or 1;

Y represents H or a residue of a C$_{1-22}$ fatty acid having the general structure (3):

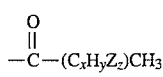 (3)

where

Z is —OH or an ether oxygen;

x is an integer of from 0 to 20;

y is an integer of from 0 to 40; and z is 0 or an integer of from 1 to 4.

Further identification of ceramide structures may be found in U.S. Pat. No. 4,950,688 (Bowser et al.), herein incorporated by reference.

Ceramides having the general structure (II) are naturally occurring and can be isolated from a suitable plant source or from animal tissue such as pig skin or neural tissue. Ceramides can also be synthesized according to procedures described in one of the following references:

Shoyama, Y. et al., *Journal of Lipid Res.*, Vol. 19, (1978), pp. 250–258.

Hino, T. et al., *Journal of Chem. Soc. Parkin. Tran. J.* (1986), p. 1687.

Junana, R. et al., *Hel. Chem. Acta,* Vol. 69(1986), p. 368.

Kiso, M. et al., *J. Carbohydrate Chem.*, Vol. 5, (1986), p. 93.

Kolke, K. et al., *Carbohyd. Res.*, Vol. 158, (1986), p. 113.

Schmidt, R. et al., *Tetrahedro. Let.,* (1986), pp. 481.

Ceramides may also be mixtures of different stereo isomers. Preferred examples of ceramides are short to medium chain ceramides, ceramide 2 and ceramide 3, as depicted by Formulae K and L below. Most preferred, in order to attain the synergy with 25-OH-D$_3$ are short chain ceramides wherein A=CH$_2$ or CHOH or CH=CH, R contains from 1 to 10 carbon atoms, m=0, R$_4$ is hydrogen, R$_3$ is hydrogen, R$_1$ contains from 8 to 20 carbon atoms.

Pseudoceramides

Pseudoceramides (i.e., synthetic ceramide-like structures) are preferably selected from pseudoceramides having the general structure (III):

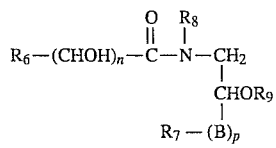 (III)

where

B represents —OCH$_2$— or —CHCHOH or —CH$_2$;

R$_6$ represents a linear or branched, saturated or unsaturated, hydroxylated or non-hydroxylated aliphatic hydrocarbon group having from 1 to 49 carbon atoms or the subgroup (2) as described above;

R$_7$ represents a linear or branched, saturated or unsaturated, hydroxylated or non-hydroxylated hydrocarbon group having from 8 to 28 carbon atoms or a phenyl group;

$R_8$ represents H, or a subgroup —$(CH_2)_cR_{10}$, or a subgroup having the structure (4), where c is an integer of from 1 to 6, $R_{10}$ is —OH or a phosphate group, or a sulfate group, or a sugar group;

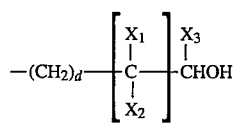

(4)

where $X_1$, $X_2$ and $X_3$ each individually represent H, a $C_{1-5}$ alkyl or a $C_{1-5}$ hydroxyalkyl;

d is 0 or an integer of from 1 to 4;

e is 0 or 1;

n is 0 or 1; and p is 0 or 1;

$R_9$ represents H, a phosphate group, a sulphate group or a sugar group.

Pseudoceramides may be synthesized according to the procedures described in U.S. Pat. No. 4,778,823 or U.S. Pat. No. 5,198,210, or U.S. Pat. No. 5,206,020, all of which are incorporated by reference herein.

Preferably, in order to attain synergy and minimize cost, pseudoceramides are employed wherein $R_6$ contains from 1 to 16 carbon atoms. Most preferably, $R_6$ contains from 1 to 10 carbon atoms, m=0, $R_8$ is $CH_2CH_2OH$, $R_9$ is hydrogen, B is —$OCH_2$ or $CH_2$, and $R_7$ contains from 10 to 22 carbon atoms.

Neoceramides

Neoceramides, like pseudoceramides, are synthetic ceramide-like structures. Neoceramides, however, contain more localized polar groups than pseudoceramides. Neoceramides are selected from neoceramides having the general structure (IV).

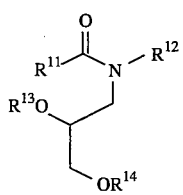

(IV)

wherein $R^{11}$ is a linear or branched, saturated, or unsaturated, aliphatic hydrocarbon group having from 1 to 50 carbon atoms which may contain a hydroxy group, ester group and/or an ether group; $R^{12}$ is a linear branched, saturated or unsaturated aliphatic hydrocarbon group having from 7 to 48 carbon atoms; $R^{13}$ and $R^{14}$ are the same or different and each is selected from the group consisting of hydrogen, a sulfate group, a phosphate group, or a sugar group.

The neoceramide can be prepared in two steps: first, neosphingosine of formula (V) is prepared by reacting halopropanediol or glycidol with an alkylamine ($R^{12}NH_2$). In a preferred embodiment of the invention, the alkylamine is preferably a primary amine and it contains from 1 to 48, preferably from 7 to 26, most preferably from 11 to 18 carbon atoms.

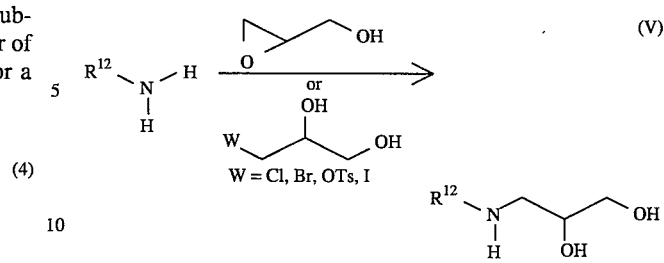

(V)

When glycidol is employed, 0.8–2.0 equivalents, preferably 1.0 equivalent, of glycidol is added, slowly to the stirring mix of one equivalent of the alkylamine in a solvent. Suitable solvents include but are not limited to ethanol, methanol, isopropanol or water; the reaction may also be performed neat. The mixture is preferably heated, preferably from 25°–100° C., for a sufficient time, e.g. 1–48 hours. After the completion of the reaction, neosphingosine is isolated. When halopropanediol (one equivalent)is employed, suitable halopropanediols include but are not limited to bromopropanediol, chloropropanediol, 3-tosylpropanediol and iodopropanediol, is reacted with preferably one equivalent of alkylamine in presence of 1–3 equivalent of base (e.g., potassium carbonate, etc.,) in a solvent. The same solvent may be employed as described above. A similar work up is employed to isolate neosphingosine of formula V.

$$R^{12}\diagdown\underset{H}{N}\diagup\diagdown\underset{OH}{\phantom{O}}\diagup\diagdown OH \longrightarrow$$

(V)

$$R^{11}\diagdown\underset{\phantom{O}}{\overset{O}{C}}\diagdown\underset{\phantom{O}}{N}\diagup R^{12}$$
$$R^{13}O\diagdown\phantom{OR^{12}}$$
$$\phantom{R^{13}O}\diagdown OR^{12}$$

(IV)

The resulting neosphingosine of formula V may be converted into a neoceramide of formula IV by reacting the neosphingosine with an acyl chloride, acyl anhydride, fatty acid (with or without catalyst) or fatty acid ester.

In a preferred embodiment of the invention, $R^{11}$ is preferably a primary alkyl group containing from 1 to 16, most preferably from 1 to 10 carbons atoms, $R^{12}$ contains from 7 to 24 carbon atoms, $R^{13}$ is hydrogen and $R^{14}$ is hydrogen.

Specific preferred examples of ceramides, pseudoceramides and neoceramides are represented by the following Formulae below:

Ceramides:

(A)

$$CH_3\diagdown\underset{\phantom{O}}{\overset{O}{C}}\diagdown\underset{H}{N}\diagdown\phantom{OH}$$

$$C_{13}H_{27}\diagdown=\diagup\diagdown\underset{OH}{\phantom{O}}\diagup OH$$

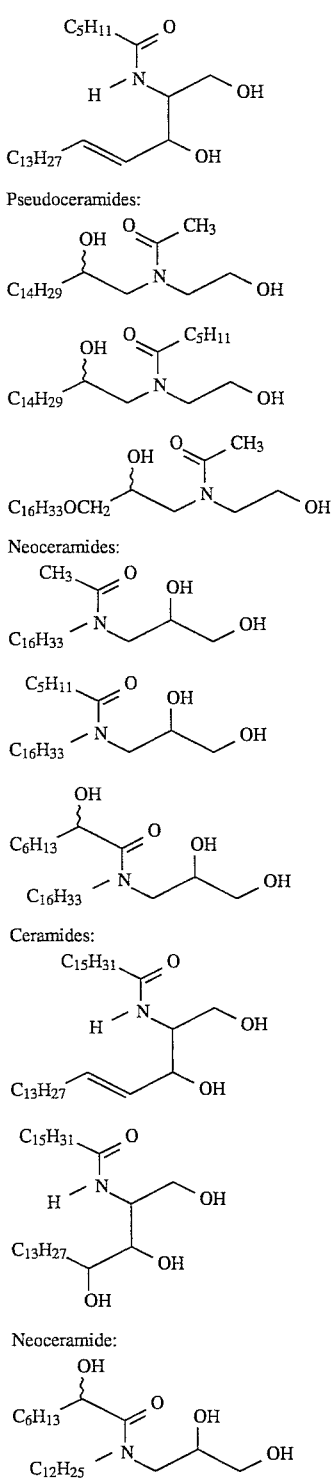

Other suitable lipids include, but are not limited to:

Ceramides

Ceramide 1, ceramide 4, ceramide 5, ceramide 6A, cerebrosides or ceramide 6B.

Pseudoceramides

N-(2-hydroxyoctadecyl)-N-(2-hydroxyethyl)hexadecanamide
N-(2-hydroxyoctadecyl)-N-(2-hydroxyethyl)propanamide
N-(2-hydroxyhexadecyl)-N-(2-hydroxyethyl)butanamide
N-(2-hydroxyhexadecyl)-N-(2-hydroxyethyl)heptanamide
N-(2-hydroxyoctadecyl)-N-(2-hydroxyethyl)ethanamide
N-(2-hydroxyoctadecyl)-N-(2-O-glucopyranosyl)ethylpentanamide
N-(2-hydroxydodecyl)-N-(2-hydroxyethyl)hexanamide
N-(2-hydroxydodecyl)-N-(2-hydroxyethyl)-2butylhexanamide
N-(2-hydroxyhexadecyl)-N-(2-hydroxyethyl)ethanamide
N-(2-hydroxydodecyl)-N-(2-hydroxyethyl)-2-hydroxyhexanamide
N-(2-hydroxytetraadecyl)-N-(2-hydroxyethyl)propanamide
N-(2-hydroxyhexadecyl)-N-(2-sulfoethyl)hexadecanamide
N-(2-hydroxyoctadecyl)-N-(2-phosphethyl)butanamide
N-(2-hydroxyoctadecyl)-N-(2-hydroxyethyl)-2-hydroxypropanamide
N-(2-hydroxydecyl)-N-(2-hydroxyethyl)butanamide
N-(2-hydroxy-3-octadecyloxypropyl)-N-(2-hydroxyethyl)hexadecanamide
N-(2-hydroxy-3-hexadecyloxypropyl)-N-(2-hydroxyethyl)hexadecanamide
N-(2-hydroxy-3-octadecyloxypropyl)-N-(2-hydroxyethyl)butanamide
N-(2-hydroxy-3-hexadecyloxypropyl)-N-(2-hydroxyethyl)ethanamide
N-(2-hydroxy-3-dodecyloxypropyl)-N-(2-sulfohydroxyethyl)decanamide
N-(2-hydroxy-3-decyloxypropyl)-N-(2-hydroxyethyl)hexanamide
N-(2-hydroxy-3-octadecyloxypropyl)-N-(2-hydroxyethyl)hexadecanamide
N-(2-hydroxy-3-dodecyloxypropyl)-N-(2-hydroxyethyl)butanamide
N-(2-hydroxy-3-octadecyloxypropyl)-N-(2-hydroxyethyl)ω-o-linoleoyldocosanamide
N-(2-hydroxy-3-dodecyloxypropyl)-N-(2-hydroxyethyl)propanamide
N-(2-hydroxy-3-decyloxypropyl)-N-(2-hydroxyethyl)-2-hydroxypropanamide
N-(2-hydroxy-3-hexadecyloxypropyl)-N-(2-hydroxyethyl)-2-methylpropanamide
N-(2-hydroxy-3-tetraadecyloxypropyl)-N-(2-hydroxyethyl)ethanamide
N-(2-hydroxy-3-nonanyloxypropyl)-N-(2-hydroxyethyl)propanamide
N-(2-hydroxy-3-dodecyloxypropyl)-N-(2-hydroxyethyl)heptanamide
N-(2-hydroxy-3-hexadecyloxypropyl)-N-(2-phosphoethyl)hexadecanamide
N-(2-hydroxy-3-dodecyloxypropyl)-N-(2-hydroxyethyl)propanamide
N-(2-hydroxy-3-octadecyloxypropyl)-N-(2-)-glucopyranosyl)ethyl-2-hydroxypropanamide
N-(2-hydroxy-3-octyloxypropyl)-N-(2-hydroxyethyl)pentanamide Neoceramides N-(2,3-dihydroxypropyl)-N-(hexadecyl)butanamide
N-(2,3-dihydroxypropyl)-N-(tetradecyl)ethanamide
N-(2,3-dihydroxypropyl)-N-(hexadecyl)-2-hydroxypropanamide
N-(2,3-dihydroxypropyl)-N-(octadecyl)butanamide
N-(2,3-dihydroxypropyl)-N-(2-ethylhexadecyl)hexanamide
N-(2,3-dihydroxypropyl)-N-(hexadecyl)-2-hydroxyoctanamide N-(2,3-dihydroxypropyl)-N-(3-methylhexadecyl)ethanamide
N-(2,3-dihydroxypropyl)-N-(dodecyl)butanamide
N-(2,3-dihydroxypropyl)-N-(hexadecyl)-2-hydroxyhexanamide
N-(2-hydroxy-3-O-glucopyranosylpropyl)-N-(hexadecyl)octanamide
N-(2-hydroxy-3-phosphopropyl)-N-(octadecyl)ethanamide
N-(2-hydroxy-3-sulfopropyl)-N-(hexadecyl)butanamide
N-(2-hydroxy-3-O-glucopyranosylpropyl)-N-(hexadecyl)decanamide
N-(2,3-dihydroxypropyl)-N-(heptadecyl)ethanamide
N-(2,3-dihydroxypropyl)-N-(3-methylhexadecyl)ethanamide
N-(2,3-dihydroxypropyl)-N-(heptadecyl)butanamide
N-(2,3-dihydroxypropyl)-N-(6-dodecenyl)hexadecanamide
N-(2,3-dihydroxypropyl)-N-(2-methylhexadecyl)2-hydroxyetahnamide
N-(2,3-dihydroxypropyl)-N-(octadecyl)2-hydroxypropanamide
N-(2-hydroxy-3-O-glucopyranosylpropyl)-N-(heptadecyl)ethanamide
N-(2-hydroxy-3-sulfopropyl)-N-(dodecyl)heptanamide
N-(2,3-dihydroxypropyl)-N-(tetradecyl)-4-hydroxybutanamide
N-(2,3-dihydroxypropyl)-N-(octadecyl)-ω-O-linoleoyl-docosanamide
N-(2,3-dihydroxypropyl)-N-(linoleyl)ethanamide
N-(2,3-dihydroxypropyl)-N-(oleyl)-2-hydroxyheptanamide
N-(2,3-dihydroxypropyl)-N-(dodecyl)-ω-O-linoleoyl-docosanamide
N-(2,3-dihydroxypropyl)-N-(octadecyl)-3-hyrdoxybutanamide
N-(2-phospho-3hydroxypropyl)-N-(heptadecyl)butanamide
N-(2,3-dihydroxypropyl)-N-(2-methylheptadecyl)propanamide
N-(2,3-dihydroxypropyl)-N-(3-ethylheptadecyl)butanamide
N-(2-sulfo-3-hydroxypropyl)-N-(1-octadecyl)ethanamide
N-(2,3-dihydroxypropyl)-N-(octadecyl)propanamide
N-(2,3-dihydroxypropyl)-N-(dodecyl)decanamide
N-(2,3-dihydroxypropyl)-N-(3-ethyldodecyl)butanamide
N-(2-O-glucopyranosyl-3-hydroxy propyl)-N-(heptadecyl)butanamide
N-(2,3-dihydroxypropyl)-N-(oleyl)-2-hydroxypropanamide
N-(2,3-dihydroxypropyl)-N-(linoleyl)-2-hydroxyheptanamide
N-(2,3-dihydroxypropyl)-N-(dodecyl)-2-hydroxyoctanamide
N-(2,3-dihydroxypropyl)-N-(hexadecyl)-2-methylheptanamide
N-(2,3-dihydroxypropyl)-N-(octadecyl)-2-hydroxypentanamide
N-(2,3-dihydroxypropyl)-N-(2-methylhexadecyl)-2-hydroxyheptanamide
N-(2,3-dihydroxypropyl)-N-(lioleyl)-2-hydroxypropanamide
N-(2,3-dihydroxypropyl)-N-(tetreadecyl)ethanamide The amount of the lipid material in the composition is in the range of from about 0.0001% to about 50% by weight of the composition, preferably from about 0.0001% to about 10%, most preferably from about 0.0001% to about 5%.

Cosmetically Acceptable Vehicle

The composition according to the invention also comprises a cosmetically acceptable vehicle to act as a dilutant, dispersant or carrier for the active components in the composition, so as to facilitate their distribution when the composition is applied to the skin, hair and/or nails.

Vehicles other than water can include liquid or solid emollients, solvents, humectants, thickeners and powders, An especially preferred nonaqueous carrier is a polydimethyl siloxane and/or a polydimethyl phenyl siloxane. Silicones of this invention may be those with viscosities ranging anywhere from about 10 to 10,000,000 centistokes at 25° C. Especially desirable are mixtures of low and high viscosity silicones. These silicones are available from the General Electric Company under trademarks Vicasil, SE and SF and from the Dow Corning Company under the 200 and 550 Series. Amounts of silicone which can be utilized in the compositions of this invention range anywhere from 5 to 95%, preferably from 25 to 90% by weight of the composition.

The cosmetically acceptable i vehicle will usually form from 5 to 99.9%, preferably from 25 to 80% by weight of the emulsion, and can, in the absence of other cosmetic adjuncts, form the balance of the composition.

Optional Skin Benefit Materials and Cosmetic Adjuncts

An oil or oily material may be present, together with an emulsifier to provide either a water-in-oil emulsion or an oil,in-water emulsion, depending largely on the average hydrophilic-lipophilic balance (HLB) of the emulsifier employed.

In a preferred embodiment of the invention, the inventive compositions further include at least one of the following ingredients which are particularly effective in combination with 25-OH-$D_3$ and the lipid component:

1. Hydroxyacids—enhance proliferation and increases ceramide biosynthesis in keratinocytes, increase epidermal thickness, and increase desquamation of normal skin resulting in smoother, younger looking skin.

The hydroxy acid can be chosen from α-hydroxy acids, β-hydroxyacids, other hydroxycarboxylic acids (e.g., dihydroxycarboxylic acid, hydroxydicarboxylic, hydroxytricarboxylic) and mixtures thereof or combination of their stereoisomers (DL, D or L).

Preferably the hydroxy acid (ii) is chosen from α-hydroxy acids having the general structure (13):

$$\overset{OH}{\underset{|}{MCHCOOH}} \quad (13)$$

where

M is H— or $CH_3(C_fH_g)_h$—, f is an integer of from 1 to 27, g is an integer of from 2 to 54, and h is 0 or 1.

Even more preferably the hydroxy acid is chosen from 2-hydroxyoctanoic acid, hydroxylauric lactic acid, and glycolic acid, and mixtures thereof. When stereo isomers exist, L-isomer is most preferred.

The keto acids can be chosen from α-keto acids, β-keto acids and mixtures thereof.

A particularly preferred α-keto acid is 2-keto octanoic acid.

Preferably the amount of the hydroxy acid component (ii) present in the composition according to the invention is from 0.01 to 20%, more preferably from 0.05 to 10% and most preferably from 0.1 to 3% by weight.

2. Retinoids—enhances keratinocyte proliferation in vitro, increases epidermal thickness and increases collagen synthesis by dermal fibroblasts. This results in protection from sun damage and smoothing of wrinkled skin. The term "retinoids" as used herein includes retinoic acid, retinol, retinal and retinol esters. Included in the term "retinoic acid" are 13-cis retinoic acid and all-trans retinoic acid.
3. Steroid hormones—inhibits inflammation and hyperproliferation of the epidermis. This results in normalization of hypersensitive skin conditions. Examples of steroid hormones include but are not limited to glucocorticoids, androgens and estrogens.
4. Essential fatty acids (EFA)—essential for the plasma membrane formation of all cells, in keratinocytes EFA deficiency makes cells hyperproliferative. Supplementation of EFA corrects this. EFAs also enhance lipid biosynthesis of epidermis and provide lipids for the barrier formation of the epidermis. The essential fatty acids are preferably chosen from linoleic acid, γ-linolenic acid, homo-γ-linolenic aid, columbinic acid, eicosa-(n-6,9,13)-trienoic acid, arachidonic acid, γ-linolenic acid, timnodonic acid, hexaenoic acid and mixtures thereof.
5. Lipid precursors—Precursors of mature lipids (mevalonic acid for cholesterol, phytosphingosine and sphingosine for ceramides and sphingolipids) supplied to the medium of keratinocytes in culture are incorporated into the mature lipids by the cells. Topically applied lipid precursors are also taken up by the skin cells and incorporated into mature barrier lipids. This would result in a better-looking skin with superior barrier function. Examples of suitable lipid precursors include but are not limited to mevalonic acid, tetracetyl phytosphingosine, sphingosine, sphinganine and ω-hydroxy fatty acids.
6. Phosphatidic acid, lysophosphotidic acid and inositol phosphates: these lipid molecules are involved in transduction of signals for growth and differentiation in keratinocytes. They play an important role in mediating the actions of cytokines and other growth factors within the skin cells. These molecules will potentially stimulate the turnover rate of the skin resulting in a younger looking skin.

Surfactants, which are also sometimes designated as emulsifiers, may be incorporated into the cosmetic compositions of the present invention. Surfactants can comprise anywhere from about 0.5 to about 30%, preferably from about 1 to about 15% by weight of the total composition. Surfactants may be cationic, nonionic, anionic, or amphoteric in nature and combinations thereof may be employed.

Illustrative of the nonionic surfactants are alkoxylated compounds based upon fatty alcohols, fatty acids and sorbitan. These materials are available, for instance, from the Shell Chemical Company under the "Neodol" designation. Copolymers of polyoxypropylene-polyoxyethylene, available under the Pluronic trademark sold by the BASF Corporation, are sometimes also useful. Alkyl polyglycosides available from the Henkel Corporation similarly can be utilized for the purposes of this invention.

Anionic-type surfactants may include fatty acid soaps, sodium lauryl sulphate, sodium lauryl ether sulphate, alkyl benzene sulphonate, mono and/or dialkyl phosphates and sodium fatty acyl isethionate.

Amphoteric surfactants include such materials as dialkylamine oxide and various types of betains (such as cocoamido propyl betaine).

Emollients are often incorporated into cosmetic compositions of the present invention. Levels of such emollients may range from about 0.5 to about 50%, preferably between about 5 and 30% by weight of the total composition. Emollients may be classified under such general chemical categories as esters, fatty acids and alcohols, polyols and hydrocarbons.

Esters may be mono- or di-esters. Acceptable examples of fatty di-esters include dibutyl adipate, diethyl sebacate, diisopropyl dimerate, and dioctyl succinate. Acceptable branched chain fatty esters include 2-ethyl-hexyl myristate, isopropyl stearate and isostearyl palmitate. Acceptable tribasic acid esters include triisopropyl trilinoleate and trilauryl citrate. Acceptable straight chain fatty esters include lauryl palmirate, myristyl lactate, oleyl eurcate and stearyl oleate. Preferred esters include coco-caprylate/caprate (a blend of coco-caprylate and coco-caprate), propylene glycol myristyl ether acetate, diisopropyl adipate and cetyl octanoate.

Suitable fatty alcohols and acids include those compounds having from 10 to 20 carbon atoms. Especially preferred are such compounds such as cetyl, myristyl, palmitic and stearyl alcohols and acids.

Among the polyols which may serve as emollients are linear and branched chain alkyl polyhydroxyl compounds, For example, propylene glycol, sorbitol and glycerin are preferred. Also useful may be polymeric polyols such as polypropylene glycol and polyethylene glycol.

Exemplary hydrocarbons which may serve as emollients are those having hydrocarbon chains anywhere from 12 to 30 carbon atoms. Specific examples include mineral oil, petroleum jelly, squalene and isoparaffins.

Another category of functional ingredients within the cosmetic compositions of the present invention are thickeners. A thickener will usually be present in amounts anywhere from 0.1 to 20% by weight, preferably from about 0.5 to 10% by weight of the composition. Exemplary thickeners are cross-linked polyacrylate materials available under the trademark Carbopol from the B. F. Goodrich Company. Gums may be employed such as xanthan, carrageenan, gelatin, karaya, pectin and locust beans gum. Under certain circumstances the thickening function may be accomplished by a material also serving as a silicone or emollient. For instance, silicone gums in excess of 10 centistokes and esters such as glycerol stearate have dual. functionality.

Various types of active ingredients may be present in cosmetic compositions of the present invention. Actives are defined as skin or hair benefit agents other than emollients and other than ingredients that merely improve the physical characteristics of the composition. Although not limited to this category, general examples include sunscreens, tanning agents, skin anti-wrinkling agents, anti-dandruff agents, anti-acne agents and hair growth stimulants.

Sunscreens include those materials commonly employed to block ultraviolet light. Illustrative compounds are the derivatives of PABA, cinnamate and salicylate. For example, octyl methoxycinnamate and 2-hydroxy-4-methoxy benzophenone (also known as oxybenzone) can be used. Octyl methoxycinnamate and 2-hydroxy-4-methoxy benzophenone are commercially available under the trademarks, Parsol MCX and Benzophenone-3, respectively. The exact amount of sunscreen employed in the emulsions can vary depending upon the degree of protection desired from the sun's UV radiation.

Additional vitamins may also be included in the compositions of the present invention. Especially preferred is vitamin A palmitate (retinyl palmitate) and vitamin E linoleate (tocopheryl linoleate). Other esters of vitamins A and E may also be utilized.

Many cosmetic compositions, especially those containing water, must be protected against the growth of potentially harmful microorganisms. Preservatives are, therefore, necessary. Suitable preservatives include alkyl esters of p-hydroxybenzoic acid, hydantoin derivatives, propionate salts, and a variety of quaternary ammonium compounds, Particularly preferred preservatives of this invention are methyl paraben, propyl paraben, imidazolidinyl urea, sodium dehydroxyacetate and benzyl alcohol. Preservatives will usually be employed in amounts ranging from about 0.5% to 2% by weight of the composition.

Powders may be incorporated into the cosmetic composition of the invention. These powders include chalk, talc, Fullers earth, kaolin, starch, smectites clays, chemically modified magnesium aluminum silicate, organically modified montmorillonite clay, hydrated aluminum silicate, fumed silica, aluminum starch octenyl succinate and mixtures thereof.

Other adjunct minor components may also be incorporated into the cosmetic compositions. These ingredients may include coloring agents, opacifiers and perfumes. Amounts of these materials may range anywhere from 0.001 up to 20% by weight of the composition.

Use of the Composition

The composition according to the invention is intended primarily as a product for topical application to human skin, especially as an agent for reducing the permeability to water of the skin, particularly when the skin is dry or damaged, in order to reduce moisture loss and generally to enhance the quality and flexibility of skin. The composition can also be applied to hair and nails.

In use, a small quantity of the composition, for example from 1 to 5 ml, is applied to exposed areas of the skin, from a suitable container or applicator and, if necessary, it is then spread over and/or rubbed into the skin using the hand or fingers or a suitable device.

Product Form and Packaging

The topical skin and/or hair treatment composition of the invention can be formulated as a lotion having a viscosity of from 4,000 to 10,000 mPas, a fluid cream having a viscosity of from 10,000 to 20,000 mPas or a cream having a viscosity of from 20,000 to 100,000 mPas or above. The composition can be packaged in a suitable container to suit its viscosity and intended use by the consumer. For example, a lotion or fluid cream can be packaged in a bottle or a roll-ball applicator or a propellant-driven aerosol device or a container fitted with a pump suitable for finger operation. When the composition is a cream, it can simply be stored in a non-deformable bottle or squeeze container, such as a tube or a lidded jar. The invention accordingly also provides a closed container containing a cosmetically acceptable composition as herein defined.

The composition may also be included in capsules such as those described in U.S. Pat. No. 5,063,507, incorporated by reference herein.

EXAMPLE 1

Example 1 demonstrates synthesis of various neoceramides (Formula IV).

Experimental

Melting points were taken on a Mel-temp in °C. and are uncorrected. Proton magnetic resonance ($^1$H NMR) spectra were recorded on a Bruker 200 MHz FT spectrometer, Varian 300 MHz FT NMR, or Varian T-60 spectrometer. Carbon magnetic resonance spectra ($^{13}$C NMR) were recorded on a Bruker 200 FT (50 MHz) spectrometer or Varian 300 MHz FT NMR. Proton and carbon chemical shifts are reported in parts per million downfield from tetramethylsilane or other silylated standard (e.g., trimethylsilypropionate sodium salt) as an internal standard. Spin multiplicities are indicated as follows: s (singlet), d (doublet), t (triplet), q (quartet), m (multiplet), or br (broad). The deuterated NMR solvents contained 99.0–99.8% deuterium in the indicated position and were purchased from the Cambridge Isotopes Laboratories. Infrared spectra (IR) were recorded on a Perkin-Elmer model 298 spectrometer and a Digilab FS 60A FTIR spectrometer using a NaCl cell or KBr solid. Peak intensities are listed as vs (very strong), s (strong), m (medium), w (weak), or br (broad) and peak positions are represented in $cm^{-1}$.

Mass spectroscopy were obtained on a Finnigan Mat SSQ710 GC/MS and on a Lee Scientific Series 600 SFC/GC connected to a Finnigan Mat TSQ70B tandem instrument.

Synthesis of N-(2,3-dihydroxypropyl)-dodecylamine (intermediate of Formula V)

Dodecylamine (25.02 g, 0.13 moles) was heated at 85° C., and glycidol (10 g, 0.13 moles) was added dropwise. The reaction was heated under nitrogen for 3 hours then allowed to stir overnight. A white solid was recovered (crude yield= 33.27 g), and the solid was recrystallized in hot hexane to give pure neosphingosine (yield=10.86 g).

m.p.: 74°–76° C.

IR (nujol film, $cm^{-1}$): 3340 (s), 3280 (m), 3000–2860 (br), 1460 (s), 1385 (m)

$^1$H NMR (200MHz, warm CDCl$_3$ with TMS): δ3.7 (br.m, 3H), 3.1 (br s, 3H), 2.6 (m, 4H), 1.5 (br m, 2H), 1.3 (br.s, 18H), 0.85 (br t, 3H)

$^{13}$C NMR (50 MHz, warm CDCl$_3$ with TMS): ppm 69.9, 65.8, 52.5, 50.0, 31.8, 30.1, 29.5, 29.2, 27.2, 22.5, 13.9 m/z (DCl/MS): 260 (M+H)$^+$.

Synthesis of N-(2,3-dihydroxypropyl)-hexadecylamine (intermediate of Formula V)

Hexadecylamine (5.00 g, 0.024 moles) was dissolved in absolute ethanol, and glycidol (3.07 g, 0.041 moles) was added dropwise. The reaction was refluxed under nitrogen for 4 hours then allowed to stir overnight. After 22 hours of refluxing, the reaction was stopped and a white solid formed during the cooling stage. The solid was recovered and recrystallized in hot hexane. (yield=2.02g)

m.p.=79°–81° C.

IR (nujol film, $cm^{-1}$): 3320 (br.s), 2920 (s), 2860 (s), 1460 (s), 1385 s $^1$H NMR (200 MHz, warm CDCl$_3$ with TMS): δ3.7 (m, 3H), 2.7 (br.s., 7H), 1.5 (m, 2H), 1.3 (br s, 26H), 0.85 (t, 3H)

$^{13}$C NMR (50 MHz, warm CDCl$_3$ with TMS): ppm 69.8, 65.8, 52.5, 50.1, 31.8, 30.1, 29.6, 29.2, 27.2, 22.6, 13.9 m/z (DCl/MS): 316.2 (M+H)$^+$.

Synthesis of N-(2,3-dihydroxypropyl)-N-(hexadecyl)-2-hydroxyoctanamide (Neoceramide of Formula H)

N-(2,3-dihydroxypropyl)-hexadecylamine (1.0 g, 3.2 mmoles) and potassium hydroxide (0.01 g, 0.18 mmoles) were heated to 85° C. under vacuum and methyl-2-hydroxyoctanoate (0.55 g, 3.2 mmoles) was added dropwise to the reaction. The reaction was heated under vacuum for 6 hours. A waxy off white solid was obtained (crude yield=1,39 g), and the waxy solid further purified by recrystallization in hot hexane. (Yield=0.88g).

m.p.: 67°–69° C.

IR (Nujol film, $cm^{-1}$): 3410 (s), 3360 (s), 2940 (vs), 2880 (vs), 1615 (s), 1480 (s), 1390 (m)

$^1$H NMR (200 MHz, $CDCl_3$ with TMS): δ2.6–4.3 (br m, 11H), 1.55 (br m, 4H), 1.25 (br s, 34H), 0.88 (br t, 6H)

$^{13}$C NMR (50 MHz, $CDCl_3$ with TMS): ppm 176.36, 70.62, 68.25, 62.61, 49.93, 48.79, 35.50, 31.89, 31.68, 30.06, 29.88, 29.66, 29.33, 28.99, 27.25, 22.66, 22.56, 14.08.

Synthesis of N-(2,3-dihydroxypropyl)-N-(dodecyl)-2-hydroxyoctnamid (Neoceramide of Formula M)

N-(2,3-dihydroxypropyl)-dodecylamine (1.0 g, 3.9 mmoles) and potassium hydroxide (0.01 g, 0.18 mmoles) were heated to 85° C. under vacuum and methyl-2-hydroxyoctanoate (0.67 g, 3.9 mmoles) was added dropwise to the reaction. The reaction was heated under vacuum for 5 hours. A waxy off white solid was obtained (crude yield=1.38 g), and the waxy solid was recrystallized in hot hexane. (Yield= 0.44 g).

m.p.: 69°–71° C.

IR (nujol film, $cm^{-1}$): 3410 (br. s), 3340 (hr. s), 2920 (s), 2860 (s), 1610 (m), 1460 (m)

$^1$H NMR (200 MHz, $CDCl_3$ with TMS): δ4.3 (m, 1H), 3.5 (m, 10H), 2.6 (m, 2H), 1.3 (br s, 28H), 0.80 (br s, 6H)

$^{13}$C NMR (50 MHz, $CDCl_3$ with TMS): ppm 176.12, 70.45, 68.21, 63.69, 49.89, 48.80, 35.38, 31.84, 31.66, 29.58, 29.49, 29.29, 28.97, 28.85, 27.23, 26.70, 25.12, 22.61, 22.53, 14.04 m/z (DCl/MS): 402.3 $(M+H)^+$.

Synthesis of N-(2,3-dihydroxypropyl)-N-(hexadecyl)ethanamide (Neoceramide of Formula F)

Acetyl chloride (1.15g. 14.8 mmoles) was added dropwise to a reactor containing N-(2,3-dihydroxypropyl)-hexadecylamine (1.5 g, 4.3 mmoles) in 3 mL of chloroform. The reaction was stirred for 16 hours at room temperature. When the reaction was completed, the, mixture was concentrated, ethanol and water was added, and the pH of the reaction was adjusted to 14. This mixture was extracted with chloroform, and organic layer was collected and concentrated. The sample was purified on a silica column chromatography to give 0.4 g of product.

m.p.: 56°–58° C.

IR (Nujol film, $cm^{-1}$): 3360 (s), 1615 (s)

$^1$H NMR (200 MHz, $CDCl_3$ with TMS): δ3.8 (br. s, 2H), 3.4 (m, 4H), 3.3 (br. m, 3H), 2.2 (s, 3H), 1.6 (br. s, 2H), 1.4 (br. s, 26H), 0.88 (br t, 3H)

$^{13}$C NMR (50 MHz, $CDCl_3$ with TMS): ppm 172.5, 70.77, 63.69, 50.1, 48.76, 31.87, 29.64, 29.51, 29.31, 28.61, 26.74, 22.62, 21.18, 14.06.

Synthesis of N-(2,3-dihydroxypropyl)-N-(hexadecyl)hexanamide (Neoceramide of Formula G)

Hexanoyl chloride (2.65g, 19.7 mmoles) was added dropwise to a reactor containing N-(2,3-dihydroxypropyl)-hexadecylamine (2.65g, 19.7 mmoles)in 8 mL of chloroform. The reaction was stirred for 16 hours at room temperature. When the reaction was completed, the mixture was concentrated, ethanol and water was added, and the pH of the reaction was adjusted to 14. This mixture was extracted with chloroform, and organic layer was collected and concentrated. The crude sample was purified on silica column chromatography to give 1.56 g of product.

m.p.: 38.8° C. (DSC)

IR (Nujol film, $cm^{-1}$): 3360 (s), 1610 (s)

$^1$H NMR (200 MHz, $CDCl_3$ with TMS): δ3.8 (br. s, 2H), 3.4 (m, 4H), 3.3 (m, 3H), 2.4 (t, 2H), 1.6 (br. m, 4H), 1.4 (br. s, 30H), 0.9 (br t, 6H)

$^{13}$C NMR (50 MHz, $CDCl_3$ with TMS): ppm 175.5, 70.9, 63.5, 49.8, 49.1, 32.9, 31.9, 31.6, 29.6, 29.5, 29.3, 28.9, 26.7, 25.11, 22.6, 22.43, 14.06, 13.9.

EXAMPLE 2

Methodology Used for Determining the Rate of DNA Synthesis in Keratinocytes After Treatment With Various Actives 1. Normal human keratinocytes isolated from neonatal foreskins by trypsin treatment were grown in DME medium/ 10% fetal calf serum in the presence of irradiated 3T3 mouse fibroblasts for establishing dividing keratinocyte colonies. Keratinocytes were grown under the above condition until their third passage.

2. For the experiments, third passage keratinocytes were plated into a serum-free keratinocyte growth medium (KGM; obtained from Clonetics Corporation, San Diego, Calif.) containing 0.15 mM calcium. 20,000 to 30,000 cells were plated into each well of 24 well cell culture plates and grown for 5 days, until the cells reach about 80% confluence.

3. Medium was changed to fresh medium and the various test materials were added to the medium from an ethanolic stock solution (10 A.M.). The final ethanol concentration in the cultures was kept below 0.2%. Control cultures received no tested material but were dosed with 0.2% ethanol. Each compound or combination was tested in three separate wells. By 4 P.M., 1 uCi of $^3$H-thymidine (AmerSham Corp., Sp activity 40 Ci/mmol) was added to the 1 ml medium in each well. The cells were incubated overnight and 24 hours later (10 A.M. next day) the amount of $^3$H-thymidine associated with the cellular DNA of keratinocytes was assessed as described below.

4. The medium was aspirated, and the wells washed with 1 ml phosphate-buffered saline. The DNA and proteins of the cells in the plate were then precipitated by adding 1 ml of ice-cold 10% trichloroacetic acid (TCA). The plates were left on ice for 30 minutes to complete the precipitation process. TCA was then aspirated and each well was then washed four times with 5% TCA. The plates were then dried on a filter pad and the cells in the wells were dissolved in 0.5 ml of 0.1N sodium hydroxide. The sodium hydroxide was then neutralized using 0.1N hydrochloric acid and the solution (1 ml total volume) was then transferred to a scintillation vial. 100 ul samples from each vial were used for protein assay using BCA protein assay reagent obtained from Pierce Chemical Company. 8 ml of a scintillation fluid (Ecolume) was added to the rest of the solution in the vial, and the vials were counted in a scintillation counter to determine the amount of radioactivity in each vial. The DNA synthesis rate was then calculated as cpm $^3$H thymidine incorporated into total cellular DNA/microgram of cell protein for each individual well. Mean and standard deviation for each group was also calculated. These numbers were also expressed as percent of control wells which did not receive any vitamin $D_3$ or vitamin $D_3$ metabolites or lipid.

5. All lipids listed in Tables 1–5 below were synthesized in-house. 25-OH-$D_3$ and 1,25-(OH)$_2$$D_3$ were obtained from Hoffman La Roche. Vitamin $D_3$ was obtained from Sigma.

6. The results that were obtained are summarized in Tables 1–5 below.

TABLE 1

Effect of 25-OH—$D_3$ or 1.25-(OH)$_2$$D_3$ Alone on DNA Synthesis of Keratinocytes

| Concentration (nM) | 25-OH—$D_3$ Test 1 | 25-OH—$D_3$ Test 2 | 25-OH—$D_3$ Test 3 | 1,25-(OH)$_2$$D_3$ Test 1 | 1,25-(OH)$_2$$D_3$ Test 2 | 1,25-(OH)$_2$$D_3$ Test 3 |
|---|---|---|---|---|---|---|
| 0 | 100 ± 4.7 | 100 ± 2.1 | 100 ± 11.4 | 100 ± 4.7 | 100 ± 2.1 | 100 ± 11.4 |
| 1 | 99.3 ± 1.9 | N.D. | N.D. | 115.3 ± 7.7 | N.D. | N. D. |
| 10 | 97.2 ± 5.9 | 86.5 ± 9.0 | 95.2 ± 6.8 | 108 ± 8.7 | 91.9 ± 5.3 | 91.8 ± 4.5 |
| 100 | 86.5 ± 5.4* | 79.1 ± 2.6* | 88.5 ± 7.2 | 102.1 ± 16.7 | 86.0 ± 7.7* | 90.3 ± 9.5 |
| 1000 | 67.8 ± 5.9* | 78.9 ± 5.4* | N.D. | 71.5 ± 2.9* | 56.3 ± 14.1* | N.D. |

*Statistically significant growth inhibition.
N.D. = Not determined

As indicated by the results in Table 1, statistically significant cell growth inhibition by both 25-OH-$D_3$ and 1,25-(OH)$_2$$D_3$ was consistently observed only at 1000 nM concentration, while cell growth inhibition was also observed at 100 nM for 25-OH-$D_3$ in two experiments and 1,25-(OH)$_2$$D_3$ in one experiment.

TABLE 2

Effect of Coramide Alone (Formula A) on DNA Synthesis of Keratinocytes

| Concentration (µM) | Test 1 | Test 2 | Test 3 |
|---|---|---|---|
| 0 | 100 ± 4.7 | 100 ± 9.9 | 100 ± 11.4 |
| 0.3 | N.D. | N.D. | 146 ± 21 |
| 1.0 | 115.1 ± 11 | 83.1 ± 6 | N.D. |
| 3.0 | N.D. | N.D. | 112 ± 13 |
| 10.0 | 105 ± 22.4 | 69.9 ± 10* | 66.0 ± 14* |

*Statistically significant growth inhibition.
N.D. = Not determined

The results in Table 2 indicate that statistically significant growth inhibition of keratinocytes with a ceramide of Formula A occurred only at the highest concentration of 10 µM (2 out of 3 experiments).

TABLE 3

Synergy Between 25-OH—$D_3$ and Ceramide (Formula A)
(Data Expressed as % of Controls)

| Concentration of 25-OH—$D_3$ (nM) | 25-OH—$D_3$ alone | 25-OH—$D_3$ 1 µM Ceramide | 25-OH—$D_3$ + 10 µM Ceramide |
|---|---|---|---|
| 1 | 100 ± 4.71 | 100 ± 9.62 | 100 ± 21.41 |
| 1 | 99.3 ± 1.91 | 78.76 ± 10.73* | 77.14 ± 7.76* |
| 10 | 97.2 ± 5.92 | 87.06 ± 4.65* | 56.94 ± 6.19* |
| 100 | 86.5 ± 5.47 | 66.81 ± 3.87* | 63.98 ± 10.98* |
| 1000 | 67.8 ± 5.92 | 66.04 ± 5.14 | 66.53 ± 4.49 |

*indicates statistically significant growth inhibition compared to the inhibition of 25-OH—$D_3$ alone.

The results in Table 3 indicate that when a combination of 25-OH-$D_3$ and a ceramide of Formula A was employed, inhibition of keratinocyte growth was observed at substantially lower concentration of 25-OH-$D_3$ (1 nM) than when 25-OH-$D_3$ was employed alone (100–1,000 nM).

TABLE 4

Synergy Between Ceramide (Formula A) and Vitamin D Metabolites

| Vitamin $D_3$ or its metabolite | No ceramide | ±3.0 µM Ceramide (Formula A) |
|---|---|---|
| 0 (ethanol vehicle only) | 100 ± 11.4 | 87.9 ± 0.8 |
| 10 nM vitamin $D_3$ | 96.4 ± 16.5 | 94.7 ± 9.9 |
| 100 nM vitamin $D_3$ | 107.4 ± 8.1 | 91.3 ± 11.5 |
| 10 nM 25-OH—$D_3$ | 95.3 ± 6.9 | 84.6 ± 11.5* |
| 100 nM 25-OH—$D_3$ | 88.5 ± 7.2 | 68.6 ± 4.4* |
| 10 nM 1,25-(OH)$_2$$D_3$ | 91.8 ± 4.6 | 75.1 ± 4.1* |
| 100 nM 1,25-(OH)$_2$$D_3$ | 90.3 ± 9.5 | 68.6 ± 10.0* |

*statistically significant growth inhibition compared to control (no ceramide).

The results shown in Table 4 indicate that when combinations of 25-OH-$D_3$ or 1,25-(OH)$_2$$D_3$ with a ceramide of Formula A were employed, significant growth inhibition was observed compared to the vitamin D metabolites alone. However, nonhydroxylated vitamin $D_3$ does not show statistically significant growth inhibition when employed alone and did not show any synergy with the ceramide in inhibiting of keratinocyte growth even when vitamin $D_3$ was included at 100 nM level.

TABLE 5

Synergy Between 25-OH—$D_3$ and Various Lipids

| Treatment | 0 nM 25-OH—$D_3$ | 10 nM 25-OH—$D_3$ | 100 nM 25-OH—$D_3$ |
|---|---|---|---|
| No ceramide | 100 ± 11.4 | 95.3 ± 6.9 | 88.5 ± 7.2 |
| 3.0 µM Ceramide (formula A) | 88.0 ± 0.8 | 84.6 ± 11.6 | 68.7 ± 4.4* |
| 3 µM neoceramide (Formula M) | 81.5 ± 6.4* | 62.9 ± 4.4* | 57.3 ± 4.4* |
| 3 µM neoceramide (Formula H) | 85.7 ± 0.9* | 90.0 ± 1.2 | 71.9 ± 2.1* |
| 3 µM neoceramide (Formula G) | 102.9 ± 12.3 | 81.4 ± 6.2* | 70.0 ± 5.1* |
| 3 µM neoceramide (Formula F) | 81.1 ± 4.9 | 74.6 ± 10.0* | 63.4 ± 4.2* |
| 3.0 µM pseudoceramide (Formula D) | 62.0 ± 12.8* | 38.9 ± 11.1* | 42.4 ± 4.3* |
| 3.0 µM pseudoceramide (Formula C) | 51.4 ± 4.0* | 39.6 ± 8.6* | 33.2 ± 3.4* |
| 3.0 µM pseudoceramide (Formula E) | 95.9 ± 22 | 80.2 ± 6.4* | 53.0 ± 22* |

*statistically significant growth inhibition.

The results in Table 5 indicate that various lipids (pseudoceramides and neoceramides) are equal to, or more potent than, ceramide of Formula A in synergistically inhibiting the 25-OH-$D_3$ mediated keratinocyte growth. In contrast to ceramide of Formula A, 3 µM neoceramides and pseudoceramides alone were growth inhibitory, but in combination with 25-OH-$D_3$ they were substantially more inhibitory.

EXAMPLE 3

Vitamin $D_3$ Metabolites' Uptake

Normal human keratinocytes were grown to confluence in Keratinocyte growth medium (KGM) containing 0.15 mM calcium. Medium was changed to fresh medium. The cells were then incubated in duplicate with 10,000 cpm (60 picomolar, or 25 picogram/ml medium) of 25-OH-$D_3$ or 1,25-$(OH)_2D_3$ for various times (0 to 240 minutes). At different time intervals indicated in the Table below, the medium of appropriate wells were aspirated, and the wells were washed three times with a 0.2% bovine serum albumin solution in 50 mM Tris/0.15M sodium chloride buffer pH 7.4. After the wash the cells in the wells were dissolved in 0.1N sodium hydroxide, neutralized with 0.1N hydrochloric acid, mixed with 5 ml of scintillation fluid (Ecolume) and counted in a beta counter. The amount of cpm associated with the cells was calculated as the percent of total cpm added for each time point studied. The results that were obtained are summarized in Table 6. Data in the table is expressed as cell associated radioactivity as % of total added. Each reported result is a mean of duplicate determinations.

TABLE 6

25-OH—$D_3$ and 1.25-$(OH)_2D_3$ Uptake by Keratinocytes

| Time (minutes) | 25-OH—$D_3$ | 1,25-$(OH)_2D_3$ |
|---|---|---|
| 0 | 2.5 | 0.8 |
| 2 | 3.2 | 2.7 |
| 5 | 0.3 | 4.2 |
| 10 | 3.4 | 13.0 |
| 15 | 8.3 | 10.0 |
| 30 | 8.1 | 20.0 |
| 60 | 6.2 | 15.6 |
| 120 | 6.8 | 26.2 |
| 240 | 9.8 | 30.8 |

As indicated by the results in Table 6 above, 1,25-$(OH)_2D_3$ was rapidly taken up by keratinocytes. By contrast, 25-OH-$D_3$ was taken up by keratinocytes at a substantially slower rate than 1,25-$(OH)_2D_3$. In addition, 1,25-$(OH)_2D_3$ up is also catabolized to inactive metabolites rapidly by keratinocytes as shown by Bikle et al. "1,25 dihydroxy vitamin $D_3$ production by human keratinocytes", *The Journal of Clinical Involv. Inc.*, Vol. 78, pp. 557–566. Therefore, exogenous application of 25-OH-$D_3$ is a better mode of delivering longer lasting steady state levels of 1,25-$(OH)_2D_3$ to skin cells.

EXAMPLE 4

This example illustrates a skin care treatment composition which preferably packaged in capsules.

SKIN CARE TREATMENT

| INGREDIENT | % w/w |
|---|---|
| Silicone Gum SE-30 | 10.00 |
| Silicone Fluid 345 | 20.00 |
| Silicone Fluid 344 | 58.39 |
| Squalene | 10.00 |
| Ceramide 3 (Formula K) | 0.01 |
| Ceramide of Formula A | 0.1 |
| 25-OH—$D_3$ | 0.001 |
| Vitamin A Palmitate | 0.50 |
| Vitamin E Linoleate | 0.50 |
| Herbal Oil | 0.50 |

EXAMPLE 5

This example also illustrates a skin care treatment composition in accordance with the invention in which the formulation of Example 1 is prepared but with the following changes:

(i) liquid paraffin is used instead of the fully hydrogenated coconut oil, and (ii) ceramide 2 (Formula L) is employed, instead of ceramide 3.

EXAMPLE 6

This example illustrates a typical skin care treatment composition within the scope of the invention.

| SKINCARE TREATMENT | |
| --- | --- |
| INGREDIENT | % w/w |
| Silicone Gum SE-30 | 10.000 |
| Silicone Fluid 345 | 20.000 |
| Silicone Fluid 344 | 57.490 |
| Squalene | 5.975 |
| Ceramide of Formula B | 1 |
| 25-OH—$D_3$ | 0.01 |
| Wheat Germ Oil | 2.000 |
| Sesame Oil | 0.500 |
| Jojoba Oil | 2.000 |
| Vitamin E Linoleate | 0.500 |
| Herbal Oil | 0.500 |
| Ceramide 1 | 0.025 |
| Vitamin A Palmitate | 0.5 |

EXAMPLE 7

This example illustrates a skin treatment system according to the present invention. Daily for two weeks, starter composition 1 is applied to the face. For a subsequent two weeks, starter composition 2 is applied daily to the face. After the fourth week, starter composition 3 is applied daily to the face for a successive two weeks. Finally, maintenance composition 4 is applied daily to the face beginning at the seventh week and continued for at least two months. Components and weight percent concentrations of the aforementioned compositions are outlined in Table 7 below.

TABLE 7

| COMPONENT | STARTER COMPOSITION SYSTEM (WEIGHT %) | | | MAINTENANCE COMPOSITION |
| --- | --- | --- | --- | --- |
| | 1 | 2 | 3 | 4 |
| L-Lactic Acid | 2.00 | 3.00 | 4.00 | 5.00 |
| Potassium L-Lactate | 0.93 | 1.41 | 1.88 | 2.34 |
| Isostearyl Neopentanoate | 36.50 | 35.01 | 33.54 | 32.08 |
| PEG-8 Caprylic/Capric Glycerides | 14.30 | 14.30 | 14.30 | 14.30 |
| Cetyl Octanoate | 12.75 | 12.75 | 12.75 | 12.75 |
| Polyglyceryl-6 Dioleate | 11.90 | 11.90 | 11.90 | 11.90 |
| Cyclomethicone | 10.17 | 10.17 | 10.17 | 10.17 |
| PPG-5-Ceteth-20 | 5.10 | 5.10 | 5.10 | 5.10 |
| Glyceryl Isostearate | 3.13 | 3.13 | 3.13 | 3.13 |
| Hydroxycaprylic Acid | 0.01 | 0.01 | 0.01 | 0.01 |
| Ceramide 3 | 0.01 | 0.01 | 0.01 | 0.01 |
| Ceramide 2 | 0.01 | 0.01 | 0.01 | 0.01 |
| Pseudoceramide of Formula C | 0.01 | 0.01 | 0.01 | 0.01 |
| 25-OH—$D_3$ | 0.0001 | 0.0001 | 0.0001 | 0.0001 |
| Water | qs | qs | qs | qs |

EXAMPLE 8

This example illustrates another treatment system according to the present invention. Daily for two weeks, starter composition 1 is applied to the face. For a subsequent two weeks, starter composition 2 is applied daily to the face. After the fourth week, starter composition 3 is applied daily to the face for a successive two weeks. Finally, maintenance composition 4 is applied daily to the face beginning at the seventh week and continued for at least two months. Components and weight percent concentrations of the aforementioned compositions are outlined in Table 8 below.

TABLE 8

| COMPONENT | STARTER COMPOSITION SYSTEM (WEIGHT %) | | | MAINTENANCE COMPOSITION |
| --- | --- | --- | --- | --- |
| | 1 | 2 | 3 | |
| Salicylic Acid | 3.10 | 5.20 | 8.00 | |
| Isopropyl Octanoate | 40.75 | 38.65 | 35.85 | |
| PEG-8 Caprylic/Capric Glycerides | 16.30 | 16.30 | 16.30 | |
| Cyclomethicone | 14.15 | 14.15 | 14.15 | |
| Sorbitan Monooleate | 10.90 | 10.90 | 10.90 | |
| Isostearic Acid | 5.34 | 5.34 | 5.34 | |
| Xanthan Gum | 0.10 | 0.10 | 0.10 | |
| Ceramide 3 | 0.01 | 0.01 | 0.01 | |
| Ceramide 2 | 0.01 | 0.01 | 0.01 | |
| Neoceramide of Formula M | 0.01 | 0.01 | 0.01 | |
| 25-OH—$D_3$ | 0.0001 | 0.0001 | 0.0001 | |
| Water | qs | qs | qs | |

EXAMPLE 9

This example illustrates an alcoholic lotion containing an amide of the invention which is suitable for application to nails.

| | % w/w |
| --- | --- |
| Neoceramide (Formula G) | 0.2 |
| 25-OH—$D_3$ | 0.002 |
| Dimethylsulphoxide | 10 |
| Ethanol | 40 |
| Antoxidant | 0.1 |
| Perfume | qs |
| Water | to 100 |

EXAMPLES 10–11

The following compositions according to the invention represent lotions which can be used in the treatment of dry, unmanageable hair.

| | % w/w | |
| --- | --- | --- |
| | 10 | 11 |
| Neoceramide (Formula M) | 1.5 | — |
| Neoceramide (Formula E) | — | 0.5 |
| 25-OH—$D_3$ | 0.015 | 0.015 |
| Perfume | 0.1 | 0.1 |
| Hydroxyethyl cellulose | 0.4 | 0.4 |
| Absolute ethanol | 25 | 25 |
| p-methyl benzoate | 0.2 | 0.2 |
| Sterilized demineralized water | to 100 | to 100 |

It should be understood that the specific forms of the invention herein illustrated and described are intended to be representative only. Changes, including but not limited to those suggested in this specification, may be made in the illustrated embodiments without departing from the clear teaching of the disclosure. Accordingly, reference should be made to the following appended claims in determining the full scope of the invention.

What is claimed is:

1. A composition for topical application to human skin, hair or nails, the composition comprising:

i) from about 0.000001 to about 10 wt. % of 25-hydroxycholecalciferol;

ii) from about 0.0001 to about 50 wt. % of a lipid material selected from the group consisting of ceramides, pseudoceramides, neoceramides, and mixtures thereof wherein ceramides have structure (II):

where A represents —CH═CH—; R is a linear, saturated aliphatic hydrocarbon group having from 1 to 10 carbon atoms; $R_1$ is a linear, saturated aliphatic hydrocarbon group having from 8 to 20 carbon atoms; $R_3$ is hydrogen; $R_4$ is a hydrogen;

pseudoceramides have the structure (III):

where $R_6$ is a linear, saturated aliphatic hydrocarbon group having from 1 to 10 carbon atoms; $R_7$ is a linear, saturated hydrocarbon group having from 10 to 22 carbon atoms; $R_9$ is hydrogen;

and neoceramides have the structure (IV):

wherein $R^{11}$ is a linear, saturated aliphatic hydrocarbon group having from 1 to 10 carbon atoms; $R^{12}$ is a linear, saturated aliphatic hydrocarbon group having from 7 to 24 carbon atoms; and iii) a cosmetically acceptable vehicle for 25-hydroxycholecalciferol and the lipid material.

2. The composition of claim 1 wherein the amount of the lipid material is from 0.0001 to 10% by weight of the composition.

3. The composition of claim 1 wherein the weight ratio of the lipid material to 25-hydroxycholecalciferol is in the range from about 1:1 to about 250:1.

4. A method of treating skin, hair, or nails which comprises applying topically thereto an effective amount of the composition of claim 1.

5. A method of improving the appearance of wrinkled, flaky, aged, photodamaged skin, the method comprising applying topically to skin an effective amount of the composition comprising i) from about 0.000001 to about 10 wt. % of 25-hydroxycholecalciferol;

ii) from about 0.0001 to about 50 wt. % of a lipid material selected from the group consisting of ceramides, pseudoceramides, neoceramides, and mixtures thereof wherein ceramides have structure (II):

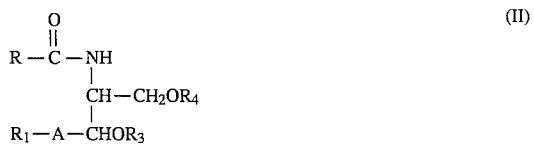

where A represents —CH═CH—; R is a linear, saturated aliphatic hydrocarbon group having from 1 to 10 carbon atoms; $R_1$ is a linear, saturated aliphatic hydrocarbon group having from 8 to 20 carbon atoms; $R_3$ is hydrogen; $R_4$ is a hydrogen;

pseudoceramides have the structure (III):

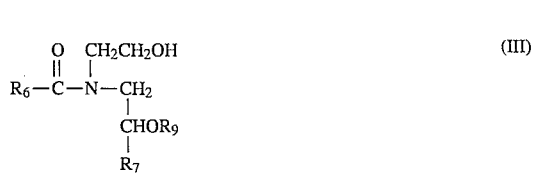

where $R_6$ is a linear, saturated aliphatic hydrocarbon group having from 1 to 10 carbon atoms; $R_7$ is a linear, saturated hydrocarbon group having from 10 to 22 carbon atoms; $R_9$ is hydrogen;

and neoceramides have the structure (IV):

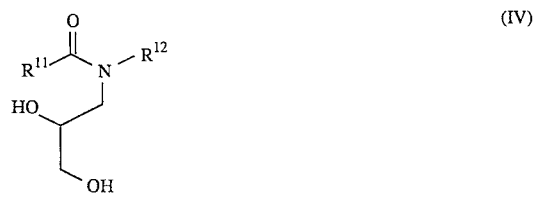

wherein $R^{11}$ is a linear, saturated aliphatic hydrocarbon group having from 1 to 10 carbon atoms; $R^{12}$ is a linear, saturated aliphatic hydrocarbon group having from 7 to 24 carbon atoms; and iii) a cosmetically acceptable vehicle for 25-hydroxycholecalciferol and the lipid material.

* * * * *